United States Patent [19]

Benkovic et al.

[11] Patent Number: 4,999,424
[45] Date of Patent: Mar. 12, 1991

[54] GAR TRANSFORMYLASE INHIBITOR

[75] Inventors: Stephen J. Benkovic, State College, Pa.; Richard A. Blatchly, Shelburne Falls, Mass.; James Inglese, E. Hanover, N.J.

[73] Assignee: The Pennsylvania State University, State College, Pa.

[21] Appl. No.: 269,510

[22] Filed: Nov. 10, 1988

[51] Int. Cl.$^5$ .................... C07H 9/06; A61K 31/70; A61K 31/395
[52] U.S. Cl. ........................................ 536/22; 536/23
[58] Field of Search ............................. 536/22; 514/42

[56] References Cited

PUBLICATIONS

Caperelli et al. (1986) J. Med. Chem. vol. 29, pp. 2117–2119.
Caperelli et al. (1987) J. Med. Chem vol. 30, pp. 1254–1256.
Jones et al. (1985) J. Med. Chem. vol. 28, pp. 1468–1476.
Taylor et al. (1985) J. Med. Chem. vol. 28, pp. 914–921.
Moran et al. (1985) Proc. Amer. Assoc. Cancer Research, vol. 26, p. 231.
Beardsley et al., "Chemistry and Biology of Pteridines, Proc. 8th International Symposium," B. A. Cooper and Whitehead, V. M., eds. (deGruyter: Berlin, pp. 953–957, 1986).
Temple et al. (1988) vol. 31, pp. 697–700.
Daubner et al. Biochemistry vol. 25, pp. 2951–2957, 1986.

Primary Examiner—John W. Rollins
Assistant Examiner—Gary L. Kunz
Attorney, Agent, or Firm—Ernest V. Linek; Donald Brown

[57] ABSTRACT

The present invention is directed to several multisubstrate adduct inhibitors of glycinamide ribonucleotide transformylase (GAR TFase; E.C. 2.1.2.2), a folate-requiring enzyme of de novo purine biosynthesis. The compounds of the present invention will be useful to provide anti-gout and/or anti-neoplastic therapeutic agents or will serve as potentiators for other such agents. The most prefefled, potent tight-binding multisubstrate adduct inhibitor of glycinamide ribonucleotide transformylase, is $N^{10}$-[5'-phosphoribosyl-1'-$\beta$-aminocarbonylmethyl-1-thioacetyl]-5,8-dideazafolate, which has the chemical formula:

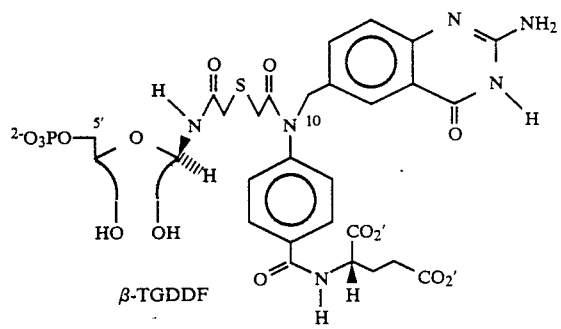

β-TGDDF

17 Claims, 1 Drawing Sheet

Fig. 1.

GAR TRANSFORMYLASE INHIBITOR

BACKGROUND OF THE INVENTION

The present invention is directed to a potent tight-binding multisubstrate adduct inhibitor of glycinamide ribonucleotide transformylase (GAR TFase; E.C. 2.1.2.2). GAR TFase is a crucial, reduced folate-requiring enzyme involved early in de novo purine biosynthesis, catalyzing the formyl transfer from (6R, alpha-S)-10-formyl H4folate to glycinamide ribonucleotide (GAR). It has thus attracted some interest as a target enzyme for the design of pharmacologically active substances, especially anti-neoplastic agents. See, Chabner, B.A., et al., in "Chemistry and Biology of Pteridines, Proc. 8th International Symposium," Cooper and Whitehead, eds. pp. 945–51, deGruyter, Berlin, 1986.

The inhibitor compounds disclosed herein will be useful as an anti-gout and/or anti-neoplastic therapeutic agent or as a potentiator for other such agents.

Specific potent inhibitors of enzymes have previously been designed using the ideas of Pauling and Jencks, which stress the importance of the enzyme's ability to stabilize a substrate's passage through its transition state to product. Much of this stabilizing energy is derived from the binding energy acquired when substrate combines with enzyme. See for example, L. Pauling, *Chem. Eng. News*, 24, 1375 (1946); W. P. Jencks, *Chemistry and Enzymology*, (Dover Publications, Inc., New York, 1987) and Gandour et al., "Transition States of Biochemical Process", (Plenum Press, New York, (1978); Collins et al., *J. Biol. Chem.*, 246, 6599–6605 (1971); Bartlett et al., *J. Am. Chem. Soc.*, 106, 4282–4283 (1984); Chan et al., *Heterocycles*, 23, 3079–3085 (1986) and Park et al., *J. Med. Chem.*, 22, 1134–1137 (1979); Wolfenden, *Annu. Rev. Biophys. Bioeng.*, 5, 271–305 (1976) and Wolfenden, *Acc. Chem. Res.*, 5, 10–18 (1972).

A number of potent specific inhibitors of enzymes have been designed using the concept of multisubstrate adduct inhibition (or MAI). See, Gandour and Schowen, eds., "Transition States of Biochemical Processes," Plenum Press, New York, 1978; and Broom, *Federation Proc.*, 45, 2779–2783 (1986). For a recent list of specific enzyme inhibitors, see Wolfenden, et al., in "Enzyme Mechanisms", Page and Williams, eds., pp. 97–102, Royal Society of Chemistry, London, 1987.

The tying together of both substrates of a bimolecular, enzyme-catalyzed reaction yields a molecule possessing the binding stabilization of both individual substrates, in addition to the entropic advantage of reduced molecularity (Jencks, W.P., *Advances in Enzymology*, 43, 219–410 (1975)). However, it should be noted that a multisubstrate adduct inhibitor is not intended to mimic the transition state of a catalyzed reaction.

The degree to which an enzyme-inhibitor complex remains associated with the desired substrate is a measure of the inhibitor's potency. A common measure for the effectiveness of an inhibitor is its dissociation constant, $K_D$, or its inhibition constant, $K_I$. To the first approximation, these are the same, and are a ratio of free inhibitor and enzyme to the enzyme inhibitor complex. The smaller the number, the less free enzyme is present, and the better the inhibitor.

Prior to the present invention, other inhibitors of GAR TFase have been produced, but none were as potent in vitro as the commonly used anti-folate agent methotrexate (which is specific for another enzyme important to purine biosynthesis, dihydrofolate reductase [DHFR]). The highly active GAR TFase inhibitor of the present invention thus represents a breakthrough in this area.

There are a modest number of compounds actually tested against GAR TFase. Those with published $K_I$ values (inhibition constants) include the work of Caperelli et al., (*J. Med. Chem.*, 29, 2117–2119 (1986) and *J. Med. Chem.*, 30, 1254–1256 (1987)) who have shown that the substitution at $N^{10}$ of DDF with various substituted alkyl, acyl, benzyl, and heterocyclic groups produce modest inhibition of murine lymphoma GAR TFase, with $K_I$'s ranging from 1.3 to 33 uM. These compounds were also shown to inhibit thymidylate synthase (TS) and dihydrofolate reductase (DHFR), illustrating a great lack of specificity for GAR TFase. See, Jones et al., *J. Med. Chem.*, 28, 1468–1476 (1985).

The inhibitor of the present invention is conservatively about $10^5$ times more potent (based on a comparison of the $K_I$ values) than the above-mentioned compounds and has no significant inhibitory effect on DHFR or TS.

DDATHF appears to be an inhibitor of GAR TFase. This inhibitor, when tested against solid tumors in mice, was indirectly shown to inhibit GAR TFase and to cause depletion of intracellular pools of ATP and GTP, end products of purine biosynthesis. See, Taylor et al., *J. Med. Chem.*, 28, 914–921 (1985); Moran et al., *Proc. Amer. Assoc. Cancer Research*, 26, 231 (1985) and Beardsley et al., "Chemistry and Biology of Pteridines, Proc. 8th International Symposium," B. A. Cooper and Whitehead, V. M., eds. (deGruyter: Berlin, pp. 953-7 (1986).

Since no data was reported for the activity of DDATHF against purified GAR TFase (i.e., there is no $K_I$ given) it is difficult to compare DDATHF to the inhibitors of the present invention in terms of potency. DDATHF appears to show impressive activity against a variety of solid tumors in mice whereas methotrexate (MTX), a common anti-folate in use today, shows minimal activity against these same tumors. Beardsley et al., *Chemistry and Biology of Pteridines*, 53–957 (1986).

None of the previously discussed inhibitors are multisubstrate adduct inhibitors. The series of DDF analogues tested by Caperelli et al., were poor inhibitors of GAR TFase both in respect to their potency and specificity. The compound of Taylor et al. may have sites of action other then GAR TFase and a quantitative account of its activity against a purified GAR TFase has yet to be reported.

Two previous attempts at the synthesis of a multisubstrate adduct inhibitor for GAR TFase have been reported. For example, Licato, Jr., in his Ph.D. Dissertation (U. Utah) reported the unsuccessful efforts toward the synthesis of the following compound:

See, *Diss. Abstr. Inc., B,* 47, 2918 (1987).

In *J. Med. Chem.,* 31, 697-700 (1988), Temple and his coworkers reported the synthesis of several potential anticancer agents which were designed to be effective as GAR TFase inhibitors. These tetrahydrofolic acid (THF) derivatives included the following:

4: $R_1 = H$; $X = O$
5: $R_1 = ClCH_2CH_2$; $X = O$
6: $R_1 = EtO_2C(CH_2)_5$; $X = O$
7: $R_1 = EtO_2C(CH_2)_6$; $X = O$
8: $R_1 = EtO_2C(CH_2)_7$; $X = O$
9: $R_1 = EtO_2C(CH_2)_8$; $X = O$

10: $R_1 = Et$; $X = S$
11: $R_1 = C_6H_5$; $X = S$
12: $R_1 = EtO_2C(CH_2)_5$; $X = S$
13: $R_1 = EtO_2C(CH_2)_6$; $X = S$
14: $R_1 = EtO_2C(CH_2)_7$; $X = S$
15: $R_1 = EtO_2C(CH_2)_8$; $X = S$

No useful biological activity was reported for any of these compounds against GAR TFase.

The synthetic approach of the present invention, has been found capable of generating the most potent and specific inhibitor of the GAR TFase enzyme yet described anywhere in the literature.

SUMMARY OF THE INVENTION

The present invention is directed to several related potent tight binding multisubstrate adduct inhibitors (MAIs) of glycinamide ribonucleotide transformylase (GAR TFase; E.C. 2.1.2.2), a folate requiring enzyme of de novo purine biosynthesis. Each of these compounds will be useful as an anti-gout, and/or anti-neoplastic therapeutic agent or as a potentiator for other such agents.

The inhibitors of the present invention have the following general Formula (I) [wherein stereochemistry, unless otherwise defined, is deemed to be variable]:

(I)

wherein R=H or $PO_3$, and pharmacologically acceptable salts thereof.

The term "pharmacologically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic, and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic anion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

Typically, the compounds of the present invention wherein R is either H or $PO_3$ are prepared as a mixture (1:1) of alpha and beta anomers (at location $C_1'$), and these mixtures are considered a part of the present invention. However, the compounds are readily separated by conventional methods and the separated compounds are considered to be preferred embodiments of the present invention.

More preferred compounds of Formula (I) are the separated alpha and beta anomers containing the phosphoribosyl group, i.e., those wherein $R = PO_3$.

The most preferred compound of Formula (I) is the beta anomer, $N^{10}$-[5'-phosphoribosyl-1'-$\beta$-amino -carbonylmethyl-1-thioacetyl]-5,8-dideazafolate, which has the stereochemical formula:

substrates, and provides the molecule with a very high specific affinity for the enzyme.

All of the inhibitors of the present invention consist of two components, a folate component and a ribonucleotide component. Each component further corresponds to a normal substrate of the enzyme. The general synthetic strategy for the formation of the compounds is illustrated in Scheme I (below).

In general, this synthetic route relies upon the synthesis of each half of the desired compound separately, and thereafter utilizes a regiospecific and mild aqueous coupling reaction to join the two halves.

For the folate half, an analogue of the natural substrate was selected, 5,8-dideazafolate (DDF, 4a) instead of the natural substrate. Activation of the DDF mole-

β-TGDDF

DETAILED DESCRIPTION OF THE PREFERRED EMBODIMENT

As described above, the present invention is most preferably directed to the beta anomer of TGDDF (for ThioGarDideazaFolate), which has the chemical name -$N^{10}$-[5'-phosphoribosyl-1'-$\beta$-aminocarbonylmethyl -1-thioacetyl]-5,8-dideazafolate.

This compound represents the first successful multisubstrate adduct inhibitor for GAR TFase which includes nearly all of the structural features of the two cule in the requisite site is readily accomplished, yielding bromoacetyl-DDF (4b).

For the ribonucleotide half, thioGAR, a GAR analogue was selected as most appropriate. The only difference between the natural substrate and thioGAR is the sulfur on the side chain in the place of a nitrogen. This provides a reactive end on thioGAR, one which allows the final coupling reaction to generate the desired compound without subsequent removal of protecting groups.

The coupling reaction itself matches the highly nucleophilic end on the thioGAR with the highly electrophilic end on bromoacetyl-DDF, (Daubner, et al., Biochem., 25, 2951-2957 (1986)).

SCHEME I

4a: R = CHO
4b: R = COCH$_2$Br

SCHEME I

α,β-TGDDF

Design and synthesis of a complementary nucleophilic GAR analog (thioGAR) allowed a convergent and regiospecific synthesis under mild conditions providing a product with inherent hydrolic and oxidative stability. The mercapto analog of GAR allowed the coupling reaction to be carried out at neutral pH in an aqueous buffered medium.

ThioGAR was prepared by the route outlined in Scheme 2, the centerpiece of which was the DCC coupling of tribenzoyl ribosylamine 5 with S-protected mercaptoacetic acid (Schendel & Stubbe, Biochem., 25: 4356–4365 (1986).

pound completely air-stable. Thirdly, the $C^6$ asymmetric center of the tetrahydrofolate has been replaced by an achiral center, again making synthetic transformations easier.

This synthesis was based in part on the previously described compound $N^{10}$-(bromoacetyl)-5,8-dideazafolate, an electrophilic irreversible inactivator of the enzyme. (Daubner, et al., Biochem., 25, 2951–2957 (1986)).

As shown in Scheme II, S-trityl mercaptoacetic acid was formed by the condensation of equimolar amounts of triphenylmethanol with mercaptoacetic acid in excess trifluoroacetic acid. Coupling of the acid with

SCHEME II

In Schemes I and II, the reagents and conditions for each of the reaction steps listed were as follows:
a: DCC, Ph$_3$CSCH$_2$CO$_2$H, acetone, RT, 14 hr.
b: NaOMe, MeOH, RT, 45 min.
c: 10 eq. POCl$_3$, (MeO)$_3$PO, 0$_o$, 2 hr.
d: 80% trifluoroacetic acid/H$_2$O, RT, 45 min.
e: Aq. NH$_3$ to pH 7.5, 100 mM HEPES, pH 7.5
f: 100 mM HEPES, pH 7.5, 60°, 1 hr.

As illustrated, the synthesis is a convergent method employing a directed coupling in aqueous solution as the last step. This avoids the deprotection problems encountered in one previously attempted synthesis of a specific MAI for GAR TFase, Licato, supra.

This synthetic scheme has several very important advantages. First, the DDF cofactor is fully active with all types of GAR TFase isolated. (Daubner et al., Biochem., 25, 2951–2957 (1986); Inglese et al., Federation Proc., 46, 2218 (1987)). Secondly, the fully oxidized, carbocyclic quinazoline ring system makes this comtribenzoyl ribosylamine, 5, was promoted by DCC. The tribenzoyl riboside, 6, was deprotected with NaOMe in MeOH, giving the water insoluble trityl thio-riboside 7. The crude riboside was phosphorylated with a 10-fold molar excess of phosphoryl chloride at 0° C. in trimethyl phosphate (Yoshikawa, et al., Tet. Lett., 50, 5065 (1967)). After hydrolytic workup, the product could be purified either by Sephadex® A-25 (Pharmacia) ion exchange chromatography, or by preparative RP-HPLC. The latter allowed separation of anomers.

Deprotection of 8 to ThioGAR, and coupling with compound 4b were accomplished in one step, using oxygen-free reagents. TritylthioGAR, 8, was treated with 1 ml of 80% aqueous TFA, then neutralized to produce a buffered pH 7.5 solution. Addition of the bromoacetyl folate derivative 4b, and reaction at 60o for one hour gave an adduct which could be purified on RP-HPLC using gradient elution (CH$_3$CN in H$_2$O.

Both solvents (12% at 0.7 ml/min.) gave pure single anomers of the adduct, with the beta anomer eluting before the alpha. The solution of pure anomer must be neutralized (aqueous NH$_3$) before concentration (Speed-vac); else in the presence of TFA, anomerization occurs.

The reaction catalyzed by GAR TFase as based on a direct displacement process is shown below in Scheme III. The two substrates in the forward direction are glycinamide ribonucleotide (GAR) and N$^{10}$-formyltetrahydrofolate (N$^{10}$—CHO—H$_4$F). In accordance with the teachings of this invention, a multisubstrate adduct inhibitor should contain sufficient characteristics of the two substrates to convey strong affinity for the target enzyme.

SCHEME III

The interaction of beta-TGDDF ($\beta$-TGDDF) with GAR TFase was characterized by the effect of the inhibitor on the activity of the enzyme as well as independent measures of its affinity for GAR TFase.

The thermodynamic dissociation constant, K$_D$, for the E.$\beta$-TGDDF complex was measured by following the enhancement of the inhibitor's 395 nm fluorescence (excitation at 275 nm) upon binding to GAR TFase. A concentrated E. coli GAR TFase solution was added to an 11 nM solution of purified $\beta$-TGDDF; for each addition, the fluorescence at three different wavelengths (396, 400, and 405 nm) was measured. Fluorescence titration data was analyzed by the method of Taira and Benkovic, *J. Med. Chem.*, 31, 129–137 (1988).

The average value for $K_D$ calculated from the three wavelengths is 250 pM, with a standard error of about 50 pM. The alpha-anomer $K_D$ is 5.8 nM, and clearly its binding affinity for GAR TFase is lower than the beta-anomer.

Beta-TGDDF acts as a slow, tight-binding inhibitor against four species of GAR TFase; *E. coli*, Avian, HeLaO, and L1210. All assays were carried out by following the increase of 5,8-dideazafolate absorbence at 295 nm in buffered medium at 26° C. To initiate the reaction, enzyme (1 nM final concentration) was added to a mixture of saturating substrates and variable amounts of inhibitor. A characteristic family of curves was obtained, showing slow, tight-binding inhibition. See, Morrison, *Trends Biochem. Sc.*, 7, 102 (1982) and Morrison, et al., *Adv. Enzymology, Relat. Areas Mol. Biol.*, 57, 201–301 (1987).

As has been described above, the compounds of the present invention are useful for inhibiting the GAR TFase enzyme in animals, including humans. The invention thus further provides a method for the inhibition of this enzyme in animals, including mammals, and especially humans, which comprises the administration of a clinically useful amount of a compound of Formula (I) in a pharmaceutically useful form, once or several times a day or other appropriate schedule, orally, rectally, parenterally, or applied topically.

Thus there is provided as a further, or alternative aspect of the invention, the compounds of the present invention for use in therapy, as GAR TFase inhibitors. For example, it is believed that the compounds of the present invention, as effective inhibitors of the GAR TFase enzyme in vivo, will be useful in the treatment and/or prevention of gout in patients suffering from inherited superactivity of PRPP synthetase. See, M. A. Becker et al., *Arthritis and Rheumatism*, Vol. 29, pp. 880–888 (1986) and M. A. Becker et al., *Biochim. Biophys. Acta*, Vol. 882, pp. 168–176 (1986).

It is further believed that enzyme inhibitors of this type are useful as anti-neoplastic therapeutic agents or as potentiators for other such agents. For example, the suspected GAR TFase inhibitor, DDATHF, has been shown to have anti-tumor activity against a wide variety of tumor cells in vivo and in vitro. These cells include inter alia; HL-60, 6C3HED lymphosarcoma, X-5563 and B-16 melanoma, and L1210 and P388 leukemia. See C. Shih et al., *Proc. Amer. Assoc. Cancer Res.*, Vol. 29, 283, Abstr. No. 1125 (1988); G. P. Beardsley et al., *Proc. Amer. Assoc. Cancer Res.*, Vol. 27, 259, Abstr. No. 1027 (1986); R. G. Moran et al., *Proc. Amer. Assoc. Cancer Res.*, Vol. 28, 274, Abstr. No. 1084 (1987); J. A. Sokoloski et al., *Proc. Amer. Assoc. Cancer Res.*, Vol. 29, 77, Abstr. No. 306 (1988); G. Pizzorno et al., *Proc. Amer. Assoc. Cancer Res.*, Vol. 29, 281, Abstr. No. 1118 (1988); E. C. Taylor et al., "Chemistry and Biology of Pteridines," pp. 116–119, Walter de Gruyter & Co., Berlin/New York (1983), E. C. Taylor et al., "Chemistry and Biology of Pteridines,"

pp. 61–64, Walter deGruyter & Co., Berlin/New York (1986), G.P. Beardsley et al., "Chemistry and Biology of Pteridines," pp. 954–957, Walter deGruyter & Co., Berlin/New York (1986), European Patent Publication No. 248,573, and PCT Patent Publication No. WO 86/05181.

The amount of compound of Formula (I) required to be effective as a therapeutic agent will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered.

A suitable effective enzyme inhibitor dose is in the range of about 0.1 to about 120 mg/kg body weight, preferably in the rang(R)of about 1.5 to 50 mg/kg, for example 10 to 30 mg/kg. The total daily dose may be given as a single dose, multiple doses, e.g., two to six times per day or by intravenous infusion for selected duration. For example, for a 75 kg mammal, the dose range would be about 8 to 9000 mg per day, and a typical dose would be about 2000 mg per day. If discrete multiple doses are indicated, treatment might typically be 500 mg of a compound of Formula (I) given 4 times per day in a pharmaceutically useful formulation.

While it is possible for the active compound (defined herein as a compound of Formula (I), or salt thereof) to be administered alone, it is preferable to present the active compound in a pharmaceutical formulation. Formulations of the present invention, for medical use, comprise the active compound together with one or more pharmaceutically acceptable carriers thereof and optionally other therapeutic ingredients. The carrier(s), must be pharmaceutically acceptable in the sense of being compatible with the other ingredients of the formulation and not deleterious to the recipient thereof.

The present invention, therefore, further provides a pharmaceutical formulation comprising one or more of the compounds of Formula (I), in the form of the free acid, ester derivative, or pharmacologically acceptable salt thereof, together with a pharmaceutically acceptable carrier therefore.

There is also provided a method for the preparation of a pharmaceutical formulation comprising bringing into association a compound of Formula (I) an ester, or pharmacologically acceptable salt thereof, and a pharmaceutically acceptable carrier therefore.

The formulations include those suitable for oral, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound in association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup; an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the Formula (I) that is isotonic with the blood of the recipient. Thus, such formulations may conveniently contain distilled water, 5% dextrose in distilled water or saline and a pharmaceutically and pharmacologically acceptable acid addition salt of a compound of the Formula (I) that has an appropriate solubility in these solvents, for example the hydrochloride, isethionate and methanesulfonate salts, preferably the latter.

Useful formulations also comprise concentrated solutions or solids containing the compound of Formula (I) which upon dilution with an appropriate solvent give a solution suitable for parenteral administration as above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

In analyzing the biological activity of the compounds of the present invention, GAR TFase from $E.$ $coli$ was used. This enzyme behaves like the mammalian and avian enzyme with respect to substrate specificity, yet is a simple and effective system having only one biological activity. That is, unlike the avian trifunctional GAR TFase, the $E.$ $coli$ species has a sole function. This follows from the genetic evidence of Smith and Daum, $J.$ $Biol.$ $Chem.,$ 262, 10565–10569 (1987) as w®11 as the work of Schrimsher et al., $Biochemistry,$ 25, 4366–4371 (1986) who have shown that AIR SYNthase from $E.$ $coli$ is a monofunctional protein, whereas, in chicken it belongs to a trifunctional protein containing, the activates: GAR SYNthase, GAR TFase, and AIR SYNthase.

The $E.$ $coli$ GAR TFase binding constants for the compounds of the present invention and other folate analogs are shown in Table I below:

TABLE I

| BINDING CONSTANTS FOR FOLATE ANALOGS WITH E. coli GAR TFase | | | |
|---|---|---|---|
| Compound | $K_D$(uM) | $K_I$(uM) | $K_m$(uM) |
| 10-CHO-DDF | — | — | 36 |
| beta-GAR | — | — | 20 |
| DDF | — | 28.1 | — |
| beta-TGDDF | $2.5 \times 10^{-4}$ | — | — |
| alpha-TGDDF | $5.8 \times 10^{-3}$ | — | — |
| alpha,beta- | | 1.7 | — |

TABLE I-continued

| BINDING CONSTANTS FOR FOLATE ANALOGS WITH E. coli GAR TFase | | | |
|---|---|---|---|
| Compound | $K_D$(uM) | $K_I$(uM) | $K_m$(uM) |
| dephospho-TGDDF | | | |

The specificity of beta-TGDDF for GAR TFase from species other than $E.$ $coli$ was assayed in a general manner by measuring the activity of GAR TFase at a concentration of 1 nM from avian, HeLa, and L1217 sources in the presence of 20 nM beta-TGDDF. All GAR TFase's were inhibited by roughly the same magnitude and all showed inhibition of a slow, tight binding nature.

Table II illustrates the specificity of beta-TGDDF for GAR TFase in comparison with other reduced-folate utilizing enzymes. This test, was conducted using the same [I]/[E]ratios as stated previously.

TABLE II

| INHIBITORY PROPERTIES OF BETA-TGDDF WITH FOLATE UTILIZING ENZYMES | |
|---|---|
| Enzyme Source | Inhibition |
| GAR TFase ($E.$ $coli$) | + |
| GAR TFase (avian) | + |
| GAR TFase (HeLa O) | + |
| GAR TFase (L1210) | + |
| AICAR TFase (avian) | — |
| DHFR ($E.$ $coli$) | — |
| DHFR (mouse) | — |
| TS ($L.$ $casei$) | — |

Figure 1:
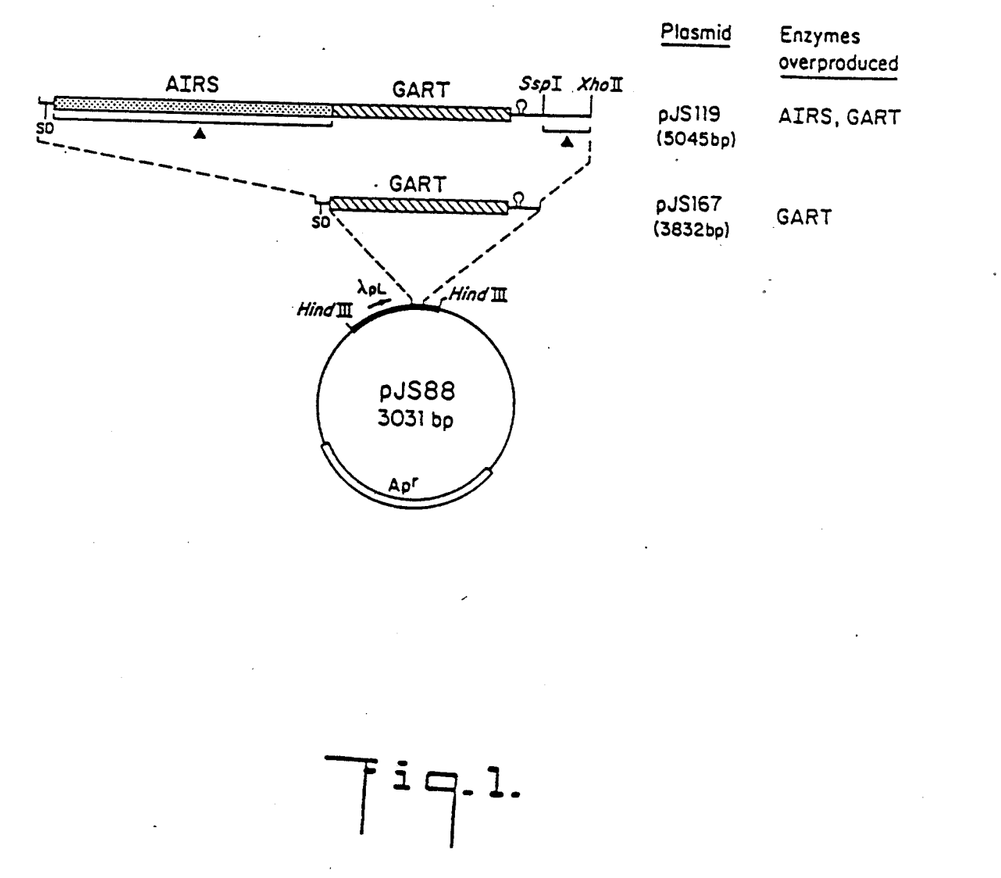
The FIGURE illustrates the preferred GAR TFase expression vector, pJS167.

This marks the first time that GAR TFase from $E.$ $coli$ has been purified to homogeneity. The enzyme was first overproduced using the high copy plasmid pJS85. The initial expression vector constructed consisted of a promoterless puMN operon cloned into the lambda pL expression vector, pJS88 to create plasmid pJSI19 (FIG. 1). Plasmid pJS88 is a lambda pL expression vector similar to those described by Remault et al., $Gene,$ 15, 81–93 (1981). Upon characterization, plasmid pJS119 was found to overproduce both AIR SYNthase (purM) and GAR TFase (purN) but the over expression of GAR TFase was not coordinate with AIR SYNthase.

Because of the non-coordinate expression of AIR SYNthase and GAR TFase in plasmid pJS119, an expression vector designed to maximize the overproduction of GAR TFase was constructed. In a series of manipulations functionally equivalent to the deletion of the AIR SYNthase (purM) coding region, plasmid pJ167 was created (FIG. 1). This expression system produces approximately 10-fold the amount of active GAR TFase per cell as pJS85.

The enzyme was first purified from the pJS85 clone using a combination of conventional chromatography separations. A final HPLC step using the Mono Q column allowed purification to greater then 95%. The same purification scheme was used for the pJS167 clone which gives from 2–8% GAR TFase per cell (based on densitometry of crude lysate) as opposed to <0.5% GAR TFase obtained from pJS85.

$E.$ $coli$ GAR TFase is a small, single subunit protein with a molecular weight of 23,212 daltons. This weight was calculated from the peptide sequence deduced from the cDNA (Smith & Daum, $J.$ $Biol.$ $Chem.,$ 262, 10565–10569 (1987)). The molecular weight of the purified protein obtained from SDS-PAGE is very close, approximately 25,000 daltons. Ultracentrifugal sedimentation velocity experiments performed on the protein under reducing and nonreducing conditions give an average molecular weight of 24,000 daltons, indicating that under the concentration and conditions studied *E. coli* GAR TFase is a monomer in solution.

The following examples are provided by the way of illustration of the present invention and should in no way be construed as a limitation thereof. All temperatures, unless otherwise indicated, are reported in degrees Celsius (°C.).

GENERAL EXPERIMENTAL PROCEDURES

All reagents were of the highest grade commercially available. Reagents for the synthesis of the inhibitor were purchased from Aldrich Chemical Co. Prostatic acid phosphatase, NADPH, dUMP, Tris, Hepes and A25-sephadex were purchased from Sigma Chemical Co.

*E. coli* GAR TFase was prepared and purified as described below. L1210 and HeLa GAR TFase were purified according to published procedures. AICAR TFase was prepared according to published procedures.

Continuous UV assays were recorded on a Beckman (Gilford) Model DUR recording quartz spectrophotometer or a Cary 219 spectrophotometer. UV spectra were recorded on a Perkin-Elmer Lamda Array 3840 UV/VIS spectrophotometer interfaced to a P & E 7300 PC. $^1$H NMR were collected on a Bruker WB-360 spectrophotometer with chemical shifts being referenced versus the transmitter offset for HDO or CHCl$_3$. All spectra taken in D$_2$O were HDO surpressed. Fluorescence spectra were recorded on an SLM Amico 8000C spectrophotometer.

HPLC was carried out on a Waters 600E with detection by a Waters 990 Photodiode Array Detector controlled by a NEC PowerMate 2 PC. HPLC columns used were either reverse phase (Perkin-Elmer/Analytical C18, 4.6 mm ID×24.5 cm) or anion exchange (Whatman Partisil 10 SAX, 4.6 mm ID×25 cm, standard analytical) unless otherwise stated.

HPLC Solvents:
Solvent A; 0.01M NH$_4$H$_2$PO$_4$,pH 3.5, 7% EtOH;
Solbent B; 1M NH$_4$H$_2$PO$_4$,pH3.5, 7% EtOH;
Solvent C; H$_2$O, 0.1% TFA;
Solvent D; CH$_3$CN, 0.07% TFA;
HPLC—Stationary and Mobile Phases:
Condition A; Anion exchange chromatography, with the following mobile phase: 100% Solvent A isocratic for 2 min. followed by a 1% per min. linear gradient to 50% Solvent B flowrate 1 ml/min., column monitoring at 238 nm.
Condition B; Reverse phase chromatography using the following mobile phase: 93% Solvent C, 7% Solvent D for 2 min. followed by a gradient from 7% to 50% D over 50 min.; flowrate 1 ml/min., column monitoring at 230 nm.
Condition C; Reverse phase chromatography using the following mobile phase: 12% Solvent D in 88% Solvent C; flowrate 0.7 ml/min., column monitoring at 230 nm.
Condition D: Reverse phase chromatography using a Whatman Partisil M9 10/50 ODS-3 column and the following mobile phase: 93% Solvent C, 7% Solvent D for 2 min. followed by a gradient from 7% to 50% D over 50 min.; flowrate 2 ml/min., column monitoring at 250 nm.

*Escherichia coli* strain TX635 (F lacZ+ cI857, (Mieschendahl & Muller-Hill, *J. Bacteriol.*, 164, 1366–1369 (1985)) contains an episome borne temperature sensitive lambda repressor and was used as a host for the lambda pL plasmids. Strains were made competent and transformed by the procedure of Dagert and Ehrlich, *Gene*, 6, 23–28 (1979). The minimal medium of Neidhardt et al., *J. Bacteriol.*, 119, 736–747 (1974) and the rich media described by Miller, *Experiments in Molecular Genetics*, pp. 1–466, Cold Spring Harbor (1972) were used for the growth of the *E. coli* K12 strains. The recombinant DNA techniques employed were those described by Tiedeman et al., *J. Biol. Chem.*, 260, 8676–8679 (1985).

EXAMPLE 1

N$^{10}$(Bromoacetyl)-5,8-Dideazafolate (DDF)

N$^{10}$-bromoacetylaton of DDF, to generate the affinity label, N$^{10}$-(bromoacetyl)-DDF, was accomplished using the method of Daubner et al., *Biochemistry*, 25, 2951-2957 (1986).

The affinity label was purified by reverse phase HPLC using a Perkin-Elmer/analytical C18 column and eluting with a linear gradient of 0.1% trifluoroacetic acid/H$_2$O and a limiting buffer of 0.08% trifluoroacetic acid/45% acetonitrile at a rate of 0.36% limiting buffer employing a flowrate of 0.7 ml/min. The peak of interest had a retention time of approximately $t_r$=55 min. Once collected, the sample was brought to dryness on a Savant Speed-Vac. The detector wavelength was 310 nm. Approximately 1 umole of material was applied to the column with each injection (typically 100 ul of a 10 mM solution in 20 mM K$_2$HPO$_4$, pH 7.5 was injected). Solutions of the affinity label were prepared in either 20 mM K$_2$HPO$_4$, pH 7.5 or 20 mM Tris, pH 7.5. The concentration was determined using the extinction coefficient $\epsilon$=4.19 mM$^{-1}$ cm$^{-1}$ for 310 nm.

EXAMPLE 2

S-Trityl Mercaptoacetic Acid

This compound was synthesized by the condensation of triphenylmethanol (2.84 g, 10.8 mmoles) with mercaptoacetic acid (0.75 ml, 10.8 mmoles) in 19 ml trifluoracetic acid. The TFA was removed in vacuo, giving an orange oil, which was purified by dissolution in ether and extraction with 1 N NaOH. The aqueous phase was acidified with 6N HCl, and extracted with two 30 ml portions of ether. The ethereal phase was dried over MgSO$_4$ and evaporated to give 3.41 g (93%) of a white solid.

NMR (CDCl$_3$)δ7.42 (m, 6H), 7.23 (m, 9H), ca. 5.2 (hr. s, 1H), 3.05 (s, 2H).

EXAMPLE 3

Tri-O-Benzoyl-N-(2-tritylmercaptoacetyl)-1-ribosylamine

To an acetone solution of 4.1 mmoles of the tri-O-benzoylribosylamine, in 80 ml acetone, was added 1.63 g (4.88 mmoles) of S-trityl-mercaptoacetic acid, followed by 1 g (4.85 mmoles) of dicyclohexylcarbodiimide (DCC). The reaction was stirred at room temperature for 14 hours, then filtered and concentrated in vacuo. The concentrated product was dissolved in 40 ml ether, filtered, washed with 30 ml each of water, 3% Na$_2$CO$_3$, and brine, and dried over Na$_2$SO$_4$. Rotary evaporation gave a white solid, which was further purified by flash chromatography on silica gel, eluting with 3% ethyl acetate in CHCl$_3$.

While anomers were separable by chromatography, the alpha/beta mixture was used in the following examples.

NMR (CDCl$_5$)δ8.05 (d, 3W), 7.95 (d, 2H), 7 (d, 2H), 76.7 2 (m, 3HO, 6.01 (dd, 1H), 5.68 (dd, 1H), 4.5 (m, 5H), 3.18 (d, 1H), 3.1 (d, 1H).

Mass Spectral Data (FAB; positive ion); 778 (10%, M+1), 536 (8%, M+1−trityl), 445 (63%, M+1−side chain), 486 (100%).

EXAMPLE 4

N-(2-tritylmercaptoacetyl)-1-ribosylamine

To a solution of tribenzoyl riboside (278 mg, 0.36 mmoles) in 5 ml absolute methanol was added 0.18 mmoles sodium methoxide in methanol and the solution was stirred at room temperature for 45 min. The resulting trityl thio-riboside was treated with Amberlite® IR-120+, filtered, concentrated by rotary evaporation and dried in a vacuum desiccator for 16 hours. Yield: 86%.

NMR (CDCl$_3$)δ7.4 (m, 6H), 7.25 (m, 9H), 7.0 (d, 1H), 5.38 (dd, 1H), 5.05 (dd, 1H), 4.1-3.65 (m, 5H), 3.05 (d, 1H), 2.97 (d, 1H).

Mass spectral data (1, CH$_4$): 2.42 (80%, trityl cation), 183 (100%, M+1−Trityl-S-H$_2$O). [The molecular ion was not apparent.]

EXAMPLE 5

5-phospho-N-(2-tritylmercaptoacetyl)-1-ribosylamine

The crude riboside from Example 4 (0.36 mmoles) was dissolved in 5 ml trimethyl phosphate, and cooled to 0°. Phosphoryl chloride (0.3 ml, 3.6 mmoles) was added over 3 min., and the reaction was stirred at 0o for 1.5 hr. To this reaction mixture was added water and 5 N NaOH sufficient for neutralization. The neutral solution was maintained at pH 7 for 1 hr. by periodic additions of 1 N NaOH, after which time it was washed with ether, and purified on a 20 ml Sephadex® A-25 chromatography (loading in 100 ml distilled water and elution with a 100 ml linear 0–500 mM NH$_4$HCO$_3$ gradient), followed by preparative HPLC (Whatman® magnum C-18 column; elution with 70% H2O/30% CH$_3$CN, with 0.1% trifluoracetic acid in each solvent). The anomers could be separated under the latter conditions, with the B-anomer eluting before the alpha-anomer. For small amounts of anomeric mixtures, the ion exchange product (contaminated by buffer and phosphate) could be loaded onto a Waters Sep-Pak in distilled water, and eluted with 30% MeOH/H$_2$O.

NMR (D$_2$O)δ7.31 ppm (d, 7.2 Hz, 6H), 7.21 (m, 9H), 4.92 (d, 4.4 Hz, 1H), 3.97 (t, 5.0 Hz, 1H), 3.85 (q, 3.7 Hz, 1HO, 3.75 (m, 2H), 3.08 (d, 15.85 Hz, 1H), 2.99 (d, 15.73 Hz, 1H).

Mass spectral data (FAB; position ion); m/e 590 (55%, M+1), 568 (45%, M-Na+H+1), 435 (53%, M-sidechain+1), 413 (65%, M-sidechain-Na+H+1).

EXAMPLE 6

N$^{10}$-[5'-phosphoribosyl-1'-β-aminocarbonylmethyl-1-thioacetyl[-5,8-dideazafolate, alpha,beta-TGDDF Deprotection of the thioGAR and coupling to N$^{10}$(bromoacetyl)-5,8-dideazafolate were accomplished in one step as follows:

The compound isolated in Example 5 (ca. 1 mg) was placed in a 10 ml rb. flask under an argon atmosphere. One ml of 80% TFA/20% H$_2$O (argon deoxygenated) was added and the mixture stirred for 45 min. at room temperature.

Treatment of an aliquot of the reaction mixture with dithionitrobenzoic acid (DTNB, Riddles et al., *Anal. Bioch.*, 94, 75–81 (1979)) allowed determination of the degree of deprotection. The reaction mixture was then cooled to Oo and 5 ml of 5 N NaOH added over 2 min. One ml of 500 mM HEPES buffer and 100 ul of 5 mM EDTA were added, and the pH was adjusted to 7.5 with 1 N NaOH. All solutions had been deoxygenated with argon.

To this mixture was added the compound of Example 1 (0.2 mg in 100 ul water); the resulting mixture was heated at 60° for one hour.

The adduct was purified on HPLC using condition B. Repurification using condition C gave pure single anomers of the adduct.

NMR spectrum of an anomeric mixture (D$_2$O);δ 7.7-7.5 (m, 3, p-phenylene and H-5), 7.42 (t, 1, H-7), 7.2-7.14 (m, 3,p-phenylene and H-8), 5.44 (d, 1, alpha-anomeric Cl'H), 5.24 (d, 1, beta-anomeric Cl'H), 4.87 (s, 2, C9-CH$_2$), 4.36 (m, 1, glutamic acid C$_{alpha}$-H), 4.2-3.7 (4, C5'CH$_2$, C2'CH), 3.21 (m, 4, CH$_2$SCH$_2$), 2.16 (t, 2, $J_{B-\gamma}$=7.4 Hz, glutamic acid C$_\gamma$—H), 1.95 (two multiplets, 2, glutamic acid C$_B$—H).

UV (50 mM HEPES, pH=7.5):λmax 230 (ε=54.5 cm$^{-1}$mM$^{-1}$),λsh 255 (ε=26.1 cm$^{-1}$mM$^{-1}$), λmax 310 (ε=4.19 cm$^{-1}$mM$^{-1}$).

EXAMPLE 7

Chemical Synthesis of Alpha/beta dephospho-TGDDF

The nonphosphorylated derivative of TGDDF was prepared using chemistry similar to that of Examples 1-6 except that thioGAR riboside was substituted for thioGAR. Purification by reverse phase HPLC, however, failed to separate the alpha and beta anomers.

EXAMPLE 8

Enzymatic Synthesis of Alpha/beta dephospho-TGDDF

To 40 ul of 50 uM solution of alpha beta-TGDDF buffered to pH 4.0 with 20 mM sodium acetate was added 4 ul of prostatic acid phosphatase (1 mg lyophilized enzyme/1 ml H$_2$O). The reaction was allowed to stir 2 hrs. at 22° after which time the solution was injected onto either anion exchange or reverse phase HPLC system using conditions A or B, respectively.

EXAMPLE 9

Construction of AIR Synthase and GAR TFase Expression Vector: pJS119

Plasmid pJSI19 (FIG. 1.) was constructed by two successive subclonings of restriction fragments that covered the nucleotide sequence 732 to 2746 (the numbering scheme refers to the published sequence (Smith and Duam, *J. Biol. Chem.*, 261, 10632-10636 (1986) and *J. Biol. Chem.*, 262, 10565-10569 (1987)) and removes the purMN promoter and purR binding site.

The first restriction fragment subcloned was a 186 bp HinPI fragment (nucleotide 732-919) treated with T4 DNA polymerase to create blunt ends and cloned into the SmaI site of M13mp18 (Yanisch-Perron et al., *Gene*, 33, 103-119 (1985)). After DNA sequencing to verify fragment identify and determine the orientation, the restriction fragment in the correct orientation to maintain purMN expression from the lac promoter was transferred to plasmid pUC18 (ibid) by restriction digest to form plasmid pJS117. The remainder of the purMN operon was added as a PpuMI-XhoII restriction fragment into the PpuMI-BamHI sites of plasmid pJS117 to form plasmid pJS118. An EcoRI-SalI restriction digest was then used to transfer the promoterless purMN operon into plasmid pJS88 to form, plasmid pJSI19 and transformed into strain TX635.

EXAMPLE 10

Construction of a GAR TFase expression vector: pJS167

This plasmid was created by a series of manipulation equivalent to the deletion of purM coding region (FIG. 1). This was accomplished by synthesizing complementary oligonucleotides which consisted of purMN sequence from the unique PpuMI site at nucleotide 770 to the purM initiation codon at nucleotide 780. The sequence continued with the purN ATG initiation codon at nucleotide 780. The sequence continued with the purN ATG initiation codon at nucleotide 1817 to the SspI site an nucleotide 1823 within th ®purN gene. This maintained the purM Shine-Dalgarno ribosome binding site in addition to introducing the ATG initiation codon of purN to replace the purM GTG initiation codon. KpnI and BamHI linkers and translational stop codons were also included in the oligonucleotide sequence to aid in cloning. After annealing of the complementary strands, the fragment was cloned into M13mp18 KpnI-BamHI sites. Colorless plaques were sequenced to verify the insert and nucleotide sequence. This fragment was then recovered by PpuMI-BamHI restriction digest and cloned into the PpuMI-BamHI sites of plasmid pJSI17 to create an intermediate plasmid pJ193. A, 747 bp SspI fragment (nucleotide 1823-2570) was then cloned into the intermediate plasmid pJS193 to reconstruct the purN coding region and creating plasmid pJS194. The modified purN gene was then transferred to plasmid pJS88 by an EcoRI-Sal/I digest to create the GAR TFase expression plasmid pJS167 in host strain TX635.

EXAMPLE 11

*E. coli GAR TFase Purification*

E. coli strain TX393 containing the multicopy plasmid pJS85 with a DNA insert containing GAR TFase (Smith and Daum, supra, was grown in M9CA media (Maniatis et al., *Molecular Cloning: A Laboratory Manual*, pp. 440–441, Cold Spring Harbor (1982)) supplemented with 30 mg/L ampicillin. Growths were started with a 1% culture inoculum and maintained at 37° C. The cells were harvested in the late log phase by centrifugation to yield typically 2.5 g/L.

E. coli strain TX635 containing either the lambda expression plasmid pJSI19 or pJS167 was grown in the rich media described above supplemented with 30 mg/L ampicillin. The cells were grown at 30° C. to confulence and then temperature jumped to 42° C. for up to 9 hours as in the case of pJS167 to obtain maximum protein production. Cells were harvested by centrifugation.

All buffers contained 50 mM Tris, pH 7.5 and 1 mM EDTA in addition to other components specified below, unless otherwise indicated. All cell manipulations were done at 4° C. unless otherwise stated.

The cells (14.6g) were resuspended in 25 ml of buffer that contained 5 mg of PMSF (carried into solution with 50 ul of DMF). The cells were disrupted by adding 38 mg of egg white lysozyme in 1 ml of buffer and 2.6 ml of Triton X100/glycerol (1.2 ml of glycerol per 50 ul of 10% Triton X100). The suspension was vortexed for 1 minute and allowed to stand at 40C for 40 minutes. The lysed cells were passed through a 17 gauge syringe 5x to shear DNA. The cell debris was removed by centrifugation at (17,000 rpm) 34,800 g for 20 minutes.

To the supernatant (-30 ml) was added 292 mg of streptomycin sulfate in 2 ml of lysis buffer via a syringe driver over 10 hrs. with gentle stirring. The milky white suspension was centrifuged at (15,000 rpm) 27,000 g for 20 minutes. The supernatant (~30 ml) was dialized (1 ½, 12,000 cut off dialyzer tubing) against 2×2.5L of buffer.

This protein solution was diluted to 150 ml with buffer and applied (~23 ml/min.) to a column of QAE A25 Sephadex (2.5×28 cm) previously equilibrated with buffer. The column was washed with buffer until the absorbance (280 nm) at the column outlet was less than 0.1 (~1L) and developed with a 2 L linear gradient of KCl (0.05 to 0.5 M KCl) in the equilibration buffer.

Fractions (~14 ml) from the QAE-Sephadex column that contained GAR TFase activity, determined by the spectrophotometric assay, that eluted at 250 mM KCl were pooled (~290 ml) and concentrated to 10 ml by using an amicon ultrafiltration apparatus with a YM10 membrane.

Half of this concentrated protein solution was applied to a column (2.5×51 cm) of Sephadex G-100 equilibrated with buffer. The flow rate was 4–5 ml/hr. Fractions (2 ml) were collected and those containing GAR TFase were pooled (22 ml) and concentrated (3 ml). This step was repeated for the remaining 5 ml of protein concentrate.

Depending on the purity of this material, as judged by densitometry of SDS-PAGE gels and reverse phase HPLC (monitored at 200 and 280 nm), an additional step was sometimes added. The >90% pure protein was further purified at room temperature (~5° C.) on a Mono Q HR5/5 column (Pharmacia, FPLC) using a linear gradient of KCl (0–50 mM) in buffer at a rate of 10% 1M KCl per min. The elution was followed at 280 nm using an in-line detector (Pharmacia). Active fractions from the center of the major peak were pooled, dialyzed against buffer, and frozen in liquid nitrogen as 1-2 mg/ml solutions.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The compounds having the Formula (I):

wherein R=H, or PO$_3$, and pharmacologically acceptable salts thereof.

2. The compounds of claim 1 wherein R=H.

3. The compound of claim 2, wherein the stereochemistry at the C$_1'$ position defines the alpha anomer.

4. The compound of claim 2, wherein the stereochemistry at the C$_1'$ position defines the beta anomer.

5. The compounds of claim 1 wherein R=PO$_3$.

6. The compound of claim 5, wherein the stereochemistry at the C$_1'$ position defines the alpha anomer.

7. The compound of claim 5, wherein the stereochemistry of the C$_1'$ position defines the data anomer.

8. A composition containing one or more of the compounds having the Formula (I):

wherein R=H, or PO$_3$, and pharmacologically acceptable salts thereof and a pharmaceutical carrier.

9. The composition of claim 8, wherein said composition comprises an effective glycinamide ribonucleotide transformylase (GAR TFase) inhibiting amount of a compound of Formula I.

10. The composition of claims 8 or 9, wherein the compounds of Formula I have R=H.

11. The composition of claim 10, wherein the stereochemistry at the C$_1'$ position in the compounds of Formula I defines the alpha anomer.

12. The composition of claim 10, wherein the stereochemistry at the C$_1'$ position in the compounds of Formula I defines the beta anomer.

13. The composition of claims 8 or 9, wherein the compounds of Formula I have R=PO$_3$.

14. The compound of claim 13, wherein the stereochemistry at the C$_1'$ position in the compounds of Formula I defines the alpha anomer.

15. The compound of claim 13, wherein the stereochemistry at the C$_1'$ position in the compounds of Formula I defines the beta anomer.

16. A method of inhibiting the enzyme glycinamide ribonucleotide transformylase (GAR TFase) in mammals including humans, which comprises administering to said mammals, a composition of claim 9.

17. A method of treating gout in mammals including humans, comprising administering to mammals in need of such treatment, an effective enzyme inhibiting amount of one or more of the compounds of having the formula:

(I)

wherein R=H, or PO$_3$,
or pharmacologically acceptable salts thereof.

* * * * *